US011134916B2

(12) United States Patent
Xu et al.

(10) Patent No.: US 11,134,916 B2
(45) Date of Patent: Oct. 5, 2021

(54) ULTRASOUND SYSTEM AND METHOD FOR DETECTING PNEUMOTHORAX

(71) Applicant: KONINKLIJKE PHILIPS N.V., Eindhoven (NL)

(72) Inventors: Jingping Xu, Shanghai (CN); Balasundar Iyyavu Raju, North Andover, MA (US); Shougang Wang, Ossining, NY (US); Mckee Dunn Poland, Andover, MA (US); Anthony M. Gades, Snohomish, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 337 days.

(21) Appl. No.: 16/066,723

(22) PCT Filed: Dec. 19, 2016

(86) PCT No.: PCT/EP2016/081629
§ 371 (c)(1),
(2) Date: Jun. 28, 2018

(87) PCT Pub. No.: WO2017/114673
PCT Pub. Date: Jul. 6, 2017

(65) Prior Publication Data
US 2019/0150889 A1 May 23, 2019

(30) Foreign Application Priority Data
Mar. 9, 2016 (EP) .................................... 16159416

(51) Int. Cl.
*A61B 8/00* (2006.01)
*A61B 8/08* (2006.01)
(52) U.S. Cl.
CPC .............. *A61B 8/4281* (2013.01); *A61B 8/08* (2013.01); *A61B 8/4254* (2013.01);
(Continued)

(58) Field of Classification Search
CPC ....... A61B 8/08; A61B 8/4254; A61B 8/4281; A61B 8/4483; A61B 8/461; A61B 8/467;
(Continued)

(56) References Cited

U.S. PATENT DOCUMENTS 5,552,645 A    9/1996 Weng
10,653,388 B2 * 5/2020 Xu ......................... G16H 50/30
(Continued)

FOREIGN PATENT DOCUMENTS

DE    10125655 A1    12/2002
JP    2010057562 A    3/2010
(Continued)

OTHER PUBLICATIONS

L. Gargani and G. Volpocelli, 'How I do it: Lung ultrasound', Cardiovascular Ultrasound, 2014, vol. 12:25 ( http://www.cardiovascularultrasound.com/content/12/1/25 ).
(Continued)

*Primary Examiner* — Amanda Lauritzen Moher (57) ABSTRACT

The invention relates to an ultrasound system (100) for sequentially performing a predetermined procedure for each of at least one region of interest. The ultrasound system (100) comprises an ultrasound probe (101) configured to transmit a first ultrasound signal (SG1) towards a region of interest and receive echo signals from the region of interest. The ultrasound system (100) also comprises a motion sensor (102) configured to detect a motion of the ultrasound probe (101) and generate a motion signal (MS) for indicating the motion of the ultrasound probe (101). The ultrasound system (100) also comprises a processor (103) configured to perform a predetermined procedure for a region of interest on the basis of the echo signals received from the region of interest if the motion signal (MS) indicates that the ultra-
(Continued)

sound probe (101) is stationary. The invention also relates to a corresponding ultrasound method.

12 Claims, 5 Drawing Sheets (52) U.S. Cl.
CPC ............ *A61B 8/4483* (2013.01); *A61B 8/461* (2013.01); *A61B 8/467* (2013.01); *A61B 8/5207* (2013.01); *A61B 8/5223* (2013.01); *A61B 8/54* (2013.01); *A61B 8/488* (2013.01)

(58) Field of Classification Search
CPC ..... A61B 8/488; A61B 8/5207; A61B 8/5223; A61B 8/54; G16H 50/30
See application file for complete search history.

(56) References Cited

U.S. PATENT DOCUMENTS

| | | | |
|---|---|---|---|
| 2002/0026118 A1* | 2/2002 | Govari | A61B 5/062 600/462 |
| 2005/0096539 A1* | 5/2005 | Leibig | A61B 8/00 600/437 |
| 2007/0078340 A1 | 4/2007 | Wilcox et al. | |
| 2010/0179428 A1* | 7/2010 | Pedersen | A61B 8/4254 600/443 |
| 2012/0108971 A1* | 5/2012 | Miyama | A61B 8/469 600/443 |
| 2012/0179035 A1 | 7/2012 | Boudier | |
| 2013/0053697 A1* | 2/2013 | Holl | G01S 7/52096 600/459 |
| 2013/0158408 A1 | 6/2013 | Tsuda et al. | |
| 2013/0184584 A1* | 7/2013 | Berkey | A61B 8/4444 600/441 |
| 2013/0197370 A1* | 8/2013 | Burlina | A61B 6/5217 600/476 |
| 2014/0128739 A1 | 5/2014 | Sundaran et al. | |
| 2014/0194742 A1 | 7/2014 | Sundaran et al. | |
| 2014/0243671 A1* | 8/2014 | Holl | A61B 8/4209 600/443 |
| 2015/0002538 A1 | 1/2015 | Sohn et al. | |
| 2015/0126869 A1* | 5/2015 | Kawabata | A61B 8/06 600/440 |
| 2015/0146855 A1* | 5/2015 | Futamura | A61B 8/4416 378/63 |
| 2015/0164482 A1* | 6/2015 | Toji | A61B 8/5276 600/443 |
| 2015/0374344 A1* | 12/2015 | Koide | G01S 7/52074 600/440 |
| 2017/0091914 A1* | 3/2017 | Halmann | A61B 8/463 |
| 2018/0344293 A1* | 12/2018 | Raju | A61B 8/54 |
| 2019/0105013 A1* | 4/2019 | Wang | G06T 7/246 |

FOREIGN PATENT DOCUMENTS

| | | |
|---|---|---|
| JP | 2012050603 A | 3/2012 |
| WO | 2016087984 A1 | 6/2016 |

OTHER PUBLICATIONS

G. Volpicelli, et al., 'International evidence-based recommendations for point-of-care lung ultrasound', Intensive Care Med., 2012, vol. 38:577-591.

M. Mennicke, et. al., 'Anatomical distribution of traumatic pneumothoraces on chest computed tomography: implications for ultrasound screening in the ED', American Journal of emergency Medicine, 2012, vol. 30: 1025-1031.

S. Kiley, et. al., 'Retrospective computed tomography mapping of intra-pleural air may demonstrate optimal window for ultrasound diagnosis of pneumothorax', Journal of Intensive Care Medicine, 2014, vol. 29: 342-347.

T. Berlet, et. al., 'Current practice of lung ultrasonography (LUS) in the diagnosis of pneumothorax: a survey of physician sonographers in Germany', Critical Ultrasound Journal, 2014, vol. 6:16. (http://www.criticalultrasoundjournal.com/content/6/1/16.

T. Berlet and R. Etter, 'Favourable experience with M-Mode sonography in the diagnosis of pneumothorax in two patients with thoracic subcutaneous emphysema', Case Report in Radiology, 2014, vol. 2014, Article ID 906127, 3 pages (http://dx.doi.org/10.1155/2014/906127 ).

BS. Ku, et. al., 'Clinician-performed bedside ultrasound for the diagnosis of pneumothorax', West Journal of Emergency Medicine, 2013, vol. 14(2):103-108.

K. Alraijhi et. al., 'Test characteristics of ultrasonography for the detection of pneumothorax: A systematic review and Meta-analysis', Chest , 2012, vol. 141(3): 703-709.

* cited by examiner

| R1 | R2 | ... | Ri | Rj | ... | Rn |
|---|---|---|---|---|---|---|
| ROI1 | ROI2 | ... | ROIi | ROIj | ... | ROIn |

| ROIi | ... | ... | ROIp | ROIq | ... | ... |
|---|---|---|---|---|---|---|
| 1 | 2 | ... | k-1 | k | ... | n |

ULTRASOUND SYSTEM AND METHOD FOR DETECTING PNEUMOTHORAX

This application is the U.S. National Phase application under 35 U.S.C. § 371 of International Application No. PCT/EP2016/081629 filed on Dec. 19, 2016, which claims the benefit of PCT/CN2015/099880 filed Dec. 30, 2015 and EP Application Serial No. 16159416.3, filed Mar. 9, 2016. These applications are hereby incorporated by reference herein.

FIELD OF THE INVENTION

The invention relates to the field of ultrasound, in particular to a system and a method for sequentially performing a predetermined procedure for each of at least one region of interest.

BACKGROUND OF THE INVENTION

Pneumothorax (PTX) is a common problem in various settings, for example, emergency care, respiratory care, interventional radiology, critical care and anaesthesia, etc. PTX represents the second most common injury after rib fracture in the domain of blunt chest trauma. Large PTXs may cause respiratory distress, and tension PTXs may cause cardiorespiratory failure. Rapid detection of PTX is important due to the life-threatening nature of these conditions.

Figure 6:
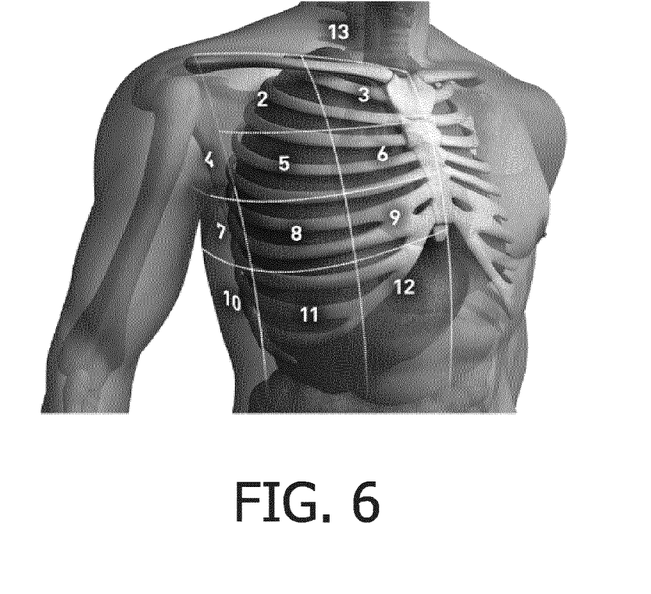
FIG. 6 illustrates an example of a plurality of regions of interest according to an embodiment of the invention.

At present, ultrasound is widely used for detection of pneumothorax (PTX). In accordance with a certain sequence defined by the clinical protocol, an ultrasound probe will be sequentially placed at various portions of the chest to detect the presence of PTX at each portion of the chest. Based on the obtained ultrasound data of each portion, the ultrasound system can analyze the ultrasound data to extract features of each portion to rule out or rule in PTX automatically. As shown in FIG. 6, there will be more than ten portions of the entire chest to be checked to determine PTX, and it will be very time-consuming if the ultrasound system cannot timely start to analyze obtained ultrasound data to determine PTX. However, if the ultrasound system start the ultrasound data analysis too early, for example, the ultrasound probe has not moved to the next portion and then the obtained ultrasound data comprise the data obtained from two portions of the chest, the analyzed result will be fully wrong. Therefore, the balance between the efficiency and accuracy is critical for providing an ultrasound system which determines when to start PTX check on each portion of multiple portions of the chest.

Figure 9:
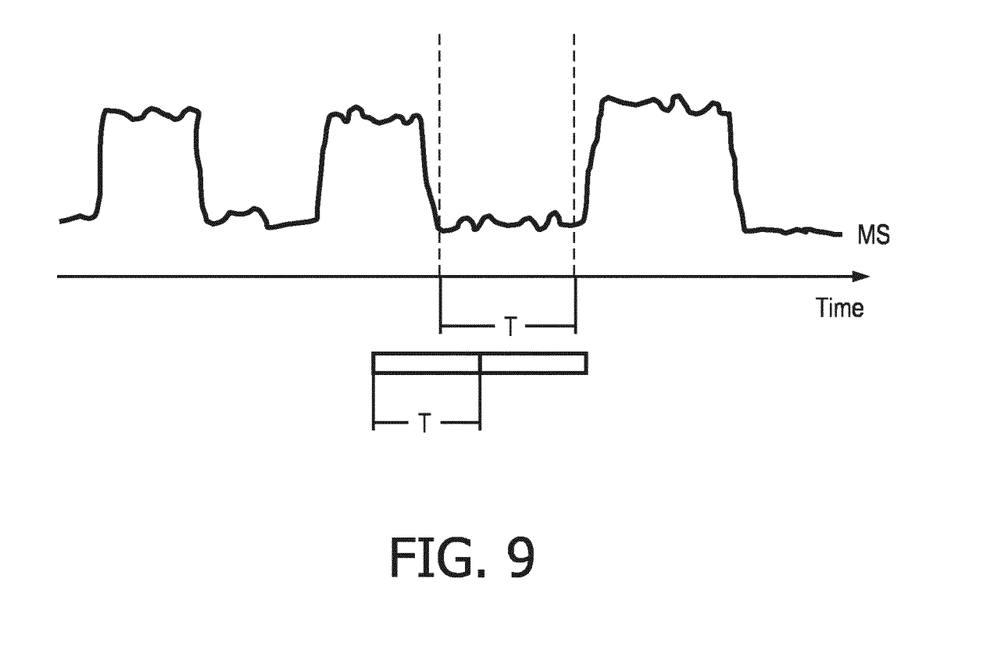
FIG. 9 illustrates an example of performing predetermined procedures according to an embodiment of the present invention.

There may be solutions which can partly solve the issue mentioned above. For example, assuming that the PTX determination on each portion will take at most time period T as shown in the upper part of FIG. 9, a proper long enough time period 2T is periodically reserved as shown in the lower part of FIG. 9 for the ultrasound system to do the PTX determination on each portion. For one more example, the solution can be obtaining the exact position information of the ultrasound probe by placing lots of markers on the subject and the ultrasound system will do PTX determination when the probe is detected on a certain portion based on the position information. However, the above two solutions may either be too time-consuming or too complex to be implemented.

US2007/0078340 A1 discloses a method and system for providing an operational command signal to a workstation of an imaging system. The workstation is provided imaging data from a positionable transducer. The method and system convert at least one of a predetermined plurality of motion patterns impacted by an operator of the system to the transducer into the operational command signal. However, US2007/0078340 A1 provides solutions to use several motion patterns to discriminate between motion intended to initiate control changes and motion which occurs normally during scanning, and it fails to provide applicable solution to solve the above mentioned issue of PTX determination which involves multiple consecutive determination on human body.

US2014/0128739 A1 discloses an ultrasound imaging system and method includes performing a gesture with a probe and detecting the gesture based on data from a motion sensing system includes at least one sensor selected from the group of an accelerometer, a gyro sensor and a magnetic sensor. However, US2014/0128739 A1 provide a solution to solve the power-consumption issue of ultrasound system and is silent about the above mentioned issue of PTX determination.

SUMMARY OF THE INVENTION

Therefore, it would be advantageous to provide an improved ultrasound system and method for sequentially performing automatic detection on different portions of a subject.

According to a first aspect of the present invention, there is proposed an ultrasound system for sequentially performing a predetermined procedure for each of at least one region of interest, comprising:

an ultrasound probe configured to transmit a first ultrasound signal towards a region of interest and receive echo signals from the region of interest;

a motion sensor configured to detect a motion of the ultrasound probe and generate a motion signal for indicating the motion of the ultrasound probe; and a processor configured to perform a predetermined procedure for a region of interest on the basis of the echo signals received from the region of interest if the motion signal indicates that the ultrasound probe is stationary.

The whole PTX determination process according to the clinical protocol may seem to be very complex due to the multiple determination processes on multiple portions of the chest. However, inventors of the present invention recognized that the operator will operate in a repeated stop-and-go mode (i.e. the operator will move the ultrasound probe to a portion of the subject, stop for a certain period on the portion and then go to the next portion) to transfer among different portions, because there is a predefined order according to the clinical protocol for all the operators to follow. The ultrasound probe will be placed on the subject by the operator without any movement, when the operator believes that the probe is ready for collecting ultrasound data for the ultrasound system to perform a predetermined procedure, such as PTX check. That is to say, the ultrasound probe will be stationary when it has been placed on the region of interest, such as a portion of the chest, by the operator and is ready for obtaining ultrasound data for check.

The motion sensor will monitor the motion of the ultrasound probe and provides motion signal indicating the motion of the probe. When the motion signal indicates that ultrasound probe is stationary, the processor will be triggered to perform a predetermined procedure, such as PTX check, on the region of interest immediately. There will be no extra time delay because the ultrasound system does not require the operator to do any extra operations to control the system to start the predetermined procedure. There is no need to place any extra devices on the region of interest, the whole system is easy to be implemented and cost effective. Furthermore, the accuracy of the solution will be good as long as the operator has been trained to follow the clinical protocol to sequentially perform the predetermined procedure for each of the at least one region of interest.

In an embodiment of the ultrasound system according to the present invention, the ultrasound probe is configured to start transmitting the first ultrasound signal if the motion signal indicates that the ultrasound probe is stationary. With this ultrasound system, the ultrasound probe is activated to start transmitting the first ultrasound signal when the ultrasound probe is detected to be stationary. The ultrasound probe is not activated when the ultrasound probe is detected to be not stationary, which saves energy and reduces ultrasound exposure.

In another embodiment of the ultrasound system according to the present invention, the ultrasound probe is configured to transmit a second ultrasound signal prior to transmitting the first ultrasound signal. This feature enables the ultrasound system to transmit the second ultrasound signal when the ultrasound probe is indicated to be not stationary. This feature allows the user access to ultrasound signals all the time. Consequently, the ultrasound signals are enabled to be visualized by the user all the time.

In an embodiment of the ultrasound system according to the present invention, the processor is further configured to generate an indication indicative of completion of the predetermined procedure. The processor enables to generate the indication timely after the predetermined procedure has been completed. The indicator indicating the condition enables providing information timely to the user. The user may move the ultrasound probe to the next region of interest in response to the indication of the indicator so as to minimize the required time spent at each region of interest.

In an embodiment of the ultrasound system according to the present invention, the ultrasound system further comprises a user interface configured to present the indication. This feature allows presenting the indication to the operator, so that the operator is aware of the completion of the predetermined procedure at the region of interest. For certain applications, the time required for performing the predetermined procedure may vary at different regions of interest. This feature allows presenting the user with timely information about the completion of the predetermined procedure at a region of interest. The user may move the ultrasound probe to the next region of interest in response to the indication so as to minimize the required time spent at each region of interest.

In an embodiment of the ultrasound system according to the present invention, the predetermined procedure for a region of interest comprises a procedure for extracting features of the region of interest from the echo signals received from the region of interest. This feature enables the ultrasound system to extract features of the region of interest automatically.

In an embodiment of the ultrasound system according to the present invention, the predetermined procedure for a region of interest comprises a procedure for detecting the presence of a pneumothorax on the basis of the echo signals received from the region of interest. This feature enables the ultrasound system to detect a pneumothorax in the region of interest automatically.

In an embodiment of the ultrasound system according to the present invention, the ultrasound system further comprises a reporting module, the processor is configured to deliver a result of the predetermined procedure for a region of interest, the reporting module is configured to identify a current region of interest of the at least one region of interest in accordance with a predetermined order of the at least one region of interest and record a result delivered by the processor as a result for the current region of interest, the at least one region of interest comprising a plurality of regions of interest. The feature applies for a plurality of regions of interest. In this way, the result of each region of interest can be recorded in sequence automatically and no extra action by the operator is required. When there are lots of regions to be checked for a certain operation, such as PTX check, the time for recording the check result of each region will be greatly reduced. The whole workflow is simple for the operator to operate, and the check result can be well recorded without any error as long as the operator does the check in the right order according to the clinical protocol.

In an embodiment of the ultrasound system according to the present invention, the ultrasound system further comprises the user interface configured to visualize the results recorded by the reporting module. This feature allows visualizing the results recorded to the user.

In an embodiment of the ultrasound system according to the present invention, the ultrasound system further comprises the user interface for receiving a user input for going back, and a go-back module configured to identify the current region of interest on the basis of the recorded results and the user input. In this way, the operator can control the check process if the operator finds something not good enough or wrong.

In an embodiment of the ultrasound system according to the present invention, the ultrasound system further comprises a position verification module configured to calculate a ratio between the size of the ultrasound acoustic shadow and the total area of a region of interest from the echo signals received from the region of interest and generate a position indicator by comparing the ratio with a predetermined threshold. Optionally, the position indicator provides information on whether the ultrasound probe is placed properly on this region of interest or needs to be placed on another region of interest.

In an embodiment of the ultrasound system according to the present invention, the motion detector is an accelerometer. With the accelerometer as the motion sensor, high accuracy measurements can be obtained.

According to a second aspect of the present invention, an ultrasound method is provided, comprising the steps of:

transmitting a first ultrasound signal towards a region of interest and receiving echo signals from the region of interest;

detecting a motion of an ultrasound probe and generating a motion signal for indicating the motion of the ultrasound probe; and performing a predetermined procedure for a region of interest on the basis of the received echo signals received from the region of interest if the motion signal indicates that the ultrasound probe is stationary.

In an embodiment of the ultrasound method according to the present invention, the ultrasound method further comprises a step of starting to transmit the first ultrasound signals if the motion signal indicates that the ultrasound probe is stationary.

In an embodiment of the ultrasound system according to the present invention, the ultrasound system further comprises a step of transmitting a second ultrasound signal prior to transmitting the first ultrasound signal.

Detailed explanations and other aspects of the invention will be given below.

BRIEF DESCRIPTION OF THE DRAWINGS

Particular aspects of the invention will now be explained with reference to the embodiments described hereinafter and considered in connection with the accompanying drawings, in which identical parts or sub-steps are designated in the same manner.

DETAILED DESCRIPTION OF THE INVENTION

The present invention will be described with respect to particular embodiments and with reference to the drawings, but the invention is not limited thereto but only by the claims. The drawings described are only schematic and are non-limiting. In the drawings, the size of some of the elements may be exaggerated and not drawn to scale for illustrative purposes.

Figure 1:
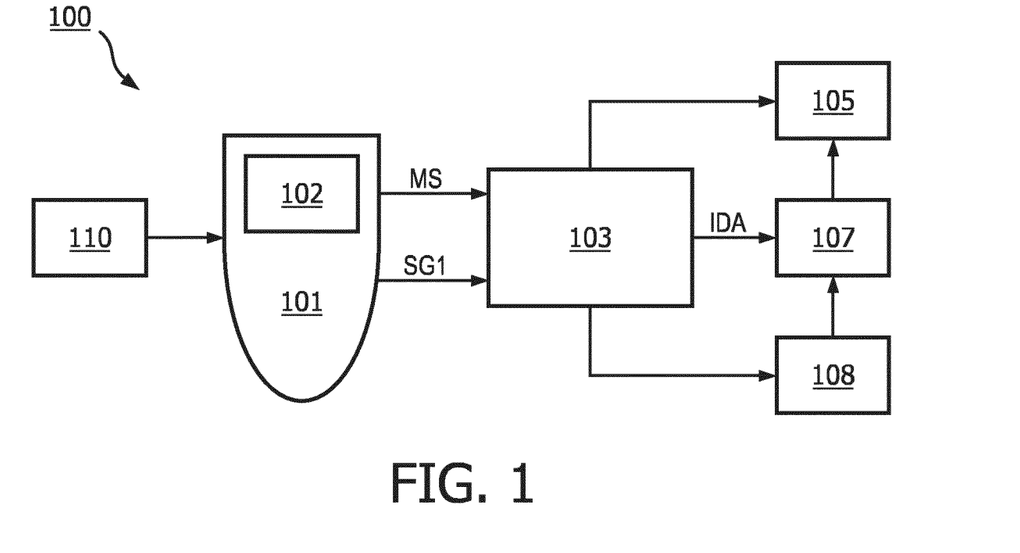
FIG. 1 schematically depicts a diagram for a system according to an embodiment of the present invention.

FIG. 1 depicts a schematic diagram of a system 100 for sequentially performing a predetermined procedure for each of at least one region of interest, according to the present invention.

The ultrasound system 100 comprises an ultrasound probe 101 configured to transmit a first ultrasound signal SG1 towards a region of interest and receive echo signals from the region of interest. The ultrasound system 100 also comprises a motion sensor 102 configured to detect a motion of the ultrasound probe 101 and generate a motion signal MS for indicating the motion of the ultrasound probe 101. The ultrasound system 100 further comprises a processor 103 configured to perform a predetermined procedure for a region of interest on the basis of the echo signals received from the region of interest if the motion signal MS indicates that the ultrasound probe 101 is stationary.

Figure 2:
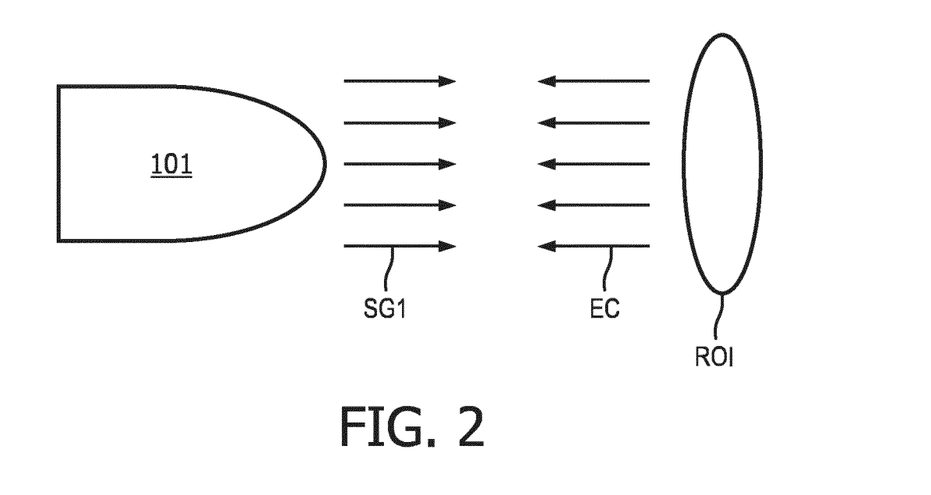
FIG. 2 illustrates an example of an ultrasound probe according to an embodiment of the present invention.

FIG. 2 illustrates an example of the ultrasound probe 101 according to an embodiment of the present invention. The ultrasound probe 101 transmits a first ultrasound signal SG1 towards a region of interest ROI. The region of interest ROI is exposed to the first ultrasound signal SG1. When the region of interest ROI reflects part of the first ultrasound signal SG1 back, the first ultrasound signal SG1's echo signal EC received from the region of interest ROI is formed. The ultrasound probe 101 receives the echo signal EC relating to the first ultrasound signal SG1 from the region of interest ROI. Therefore, the echo signal EC contains information of the region of interest ROI.

The motion sensor 102 monitors the motion of the ultrasound probe 101 and generates a motion signal MS to indicate the motion of the ultrasound probe 101. For example, accelerometers are known devices to be used as the motion sensor 102. An accelerometer may be placed on the ultrasound probe 101 to measure acceleration data of the ultrasound probe 101. Thus, accurate real-time velocity of the accelerometer can be derived on the basis of the measured data. Hence, the motion status of the ultrasound probe 101 is derived accordingly.

Gyroscopes are also known devices. They are useful for measuring or maintaining orientation, and they may be used together with the accelerometer to determine motion in 6 dimensions. There are other known devices to detect motion, such as barometer, cameras, and GPS sensor, etc. The embodiments of the motion sensor 102 are not limited to those mentioned above.

Whether the ultrasound probe 101 is stationary can be determined in many ways.

In an embodiment, it may be determined that the ultrasound probe 101 is stationary if the ultrasound probe 101's velocity derived by the motion sensor 102 is less than the minimum value which can be measured by the motion sensor 102. The minimum value of the measured data depends on the motion sensor 102's accuracy. For example, a certain type of motion sensor can only measure velocity not less than 0.0005 cm/s.

In another embodiment, there will be a maximum velocity threshold for the ultrasound probe 101 to complete the predetermined procedure, and the maximum velocity threshold may be different for different types of detection. People skilled in ultrasound detection will think that the maximum velocity threshold is small enough for determining whether the ultrasound probe 101 is stationary. It may be determined that the ultrasound probe 101 is stationary if the ultrasound probe 101's velocity derived by the motion sensor 102 is below the maximum velocity threshold. The maximum velocity threshold may be equal or larger than the minimum value which can be measured by the motion sensor 102. For example, the maximum velocity threshold is 0.0009 cm/s when the motion sensor 102 can only measure velocity not less than 0.0005 cm/s.

The motion of the ultrasound probe 101 is monitored by the motion sensor 102. When the motion sensor 102 detects that the motion of the ultrasound probe 101 is stationary as described above, the motion sensor 102 generates a motion signal MS to indicate the stationary state of the ultrasound probe 101. Then, processor 103 starts to perform a predetermined procedure for a region of interest on the basis of the echo signals received from the region of interest immediately in response to the motion signal.

Figure 3:
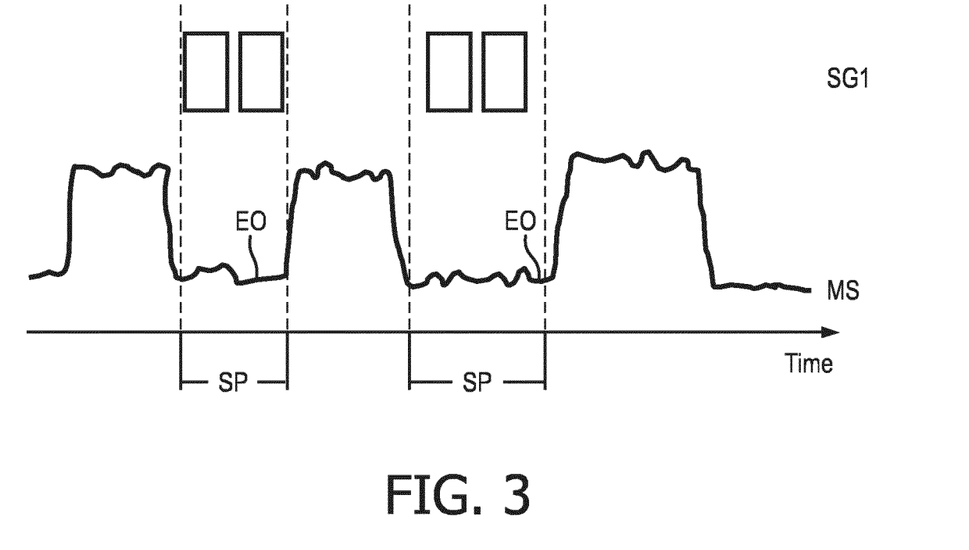
FIG. 3 illustrates an example of an ultrasound signal according to an embodiment of the present invention.

FIG. 3 illustrates an example of an ultrasound signal according to an embodiment of the present invention. In an embodiment of the invention, the ultrasound probe 101 is configured to start transmitting the first ultrasound signal SG1 if the motion signal MS indicates that the ultrasound probe 101 is stationary.

In an embodiment, an accelerometer is used to detect the motion of the ultrasound probe 101, and the motion signal MS is generated as illustrated in FIG. 3. Within the motion signal MS, there are stationary periods SP with low amplitude. When the velocity value derived from the amplitude of the stationary periods SP is less than the minimum value which can be measured by the motion sensor 102, for example, 0.0005 cm/s, the stationary periods SP indicate the stationary state of the ultrasound probe 101.

As illustrated in FIG. 3, when the motion signal MS generated from the motion sensor 102 indicates the stationary state of the ultrasound probe 101, the ultrasound probe 101 starts to transmit the first ultrasound signal SG1. The first ultrasound signal SG1 may be a sequence of ultrasound data frames. For example, the ultrasound probe 101 is activated coincidentally with the period when the motion signal MS indicates that the ultrasound probe 101 is stationary. The ultrasound probe 101 starts to transmit the first ultrasound signal SG1 when the ultrasound probe 101 is activated, i.e., when the ultrasound probe 101 is stationary.

Figure 4:
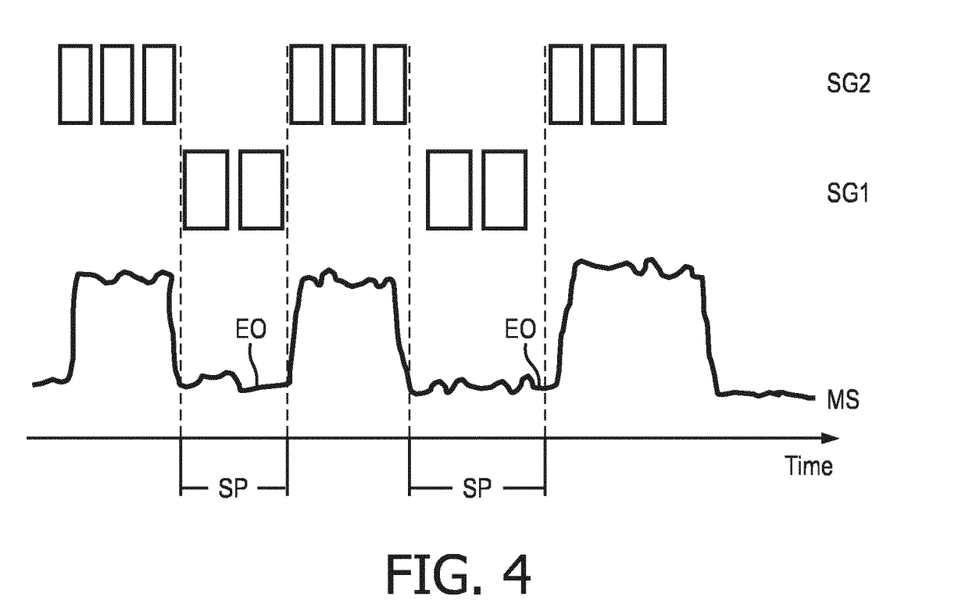
FIG. 4 illustrates another example of an ultrasound signal according to an embodiment of the present invention.

FIG. 4 illustrates another example of an ultrasound signal according to an embodiment of the present invention. In another embodiment, the ultrasound probe 101 is configured to transmit a second ultrasound signal SG2 prior to transmitting the first ultrasound signal SG1. In this embodiment, as shown in FIG. 4, the ultrasound probe 101 transmits ultrasound signals continuously. When the motion sensor 102 detects that the ultrasound probe 101 is not stationary, the ultrasound probe 101 starts to transmit the second ultrasound signal SG2. The second ultrasound signal SG2 may be a sequence of ultrasound data frames as illustrated in FIG. 4. When the motion signal indicates that ultrasound probe 101 is stationary, the ultrasound probe 101 starts to transmit the first ultrasound signal SG1 to the region of interest.

The first ultrasound signal SG1 and the second ultrasound signal SG2 are synchronized with the motion signal MS by using the same time reference system. The first ultrasound signal SG1 and the second ultrasound signal SG2 may comprise ultrasound data frames generated under many modes, such as B-mode, Doppler mode.

In another embodiment, the processor 103 is further configured to generate an indication IDA indicative of completion of the predetermined procedure.

As illustrated in FIG. 3 and FIG. 4, the completion of the predetermined procedure is denoted as E0. When the predetermined procedure is completed for the region of interest, the processor 103 generates an indication immediately.

As illustrated in FIG. 1, in another embodiment, the ultrasound image system 100 may further comprise a user interface 107 configured to present the indication IDA.

The user interface 107 aims to present an indication IDA to the operator in order to guide the operator for the next step. For example, the operator is guided to move the ultrasound probe 101 to the next region of interest. The indication IDA presented by the user interface 107 may be visible or audible to the operator. One example is a light indicator, which uses different colours of the light to indicate different types of feedback signals. Another example is an icon on a display, which visualizes the statuses to represent different types of feedback signals. An alternative example is a voice reminder, which provides audio instructions to guide the operator based on the different types of feedback signals. The embodiments of the user interface 107 are not limited to the examples mentioned above.

In another embodiment of the system 100, the predetermined procedure for a region of interest comprises a procedure for extracting features of the region of interest from the echo signals received from the region of interest.

In another embodiment of the system 100, the predetermined procedure for a region of interest comprises a procedure for detecting the presence of a pneumothorax on the basis of the echo signals received from the region of interest.

Ultrasound imaging is widely used for pneumothorax (PTX) detection. Four features have been described for PTX detection: lung sliding, B-lines, lung pulse and lung point.

Figure 5:
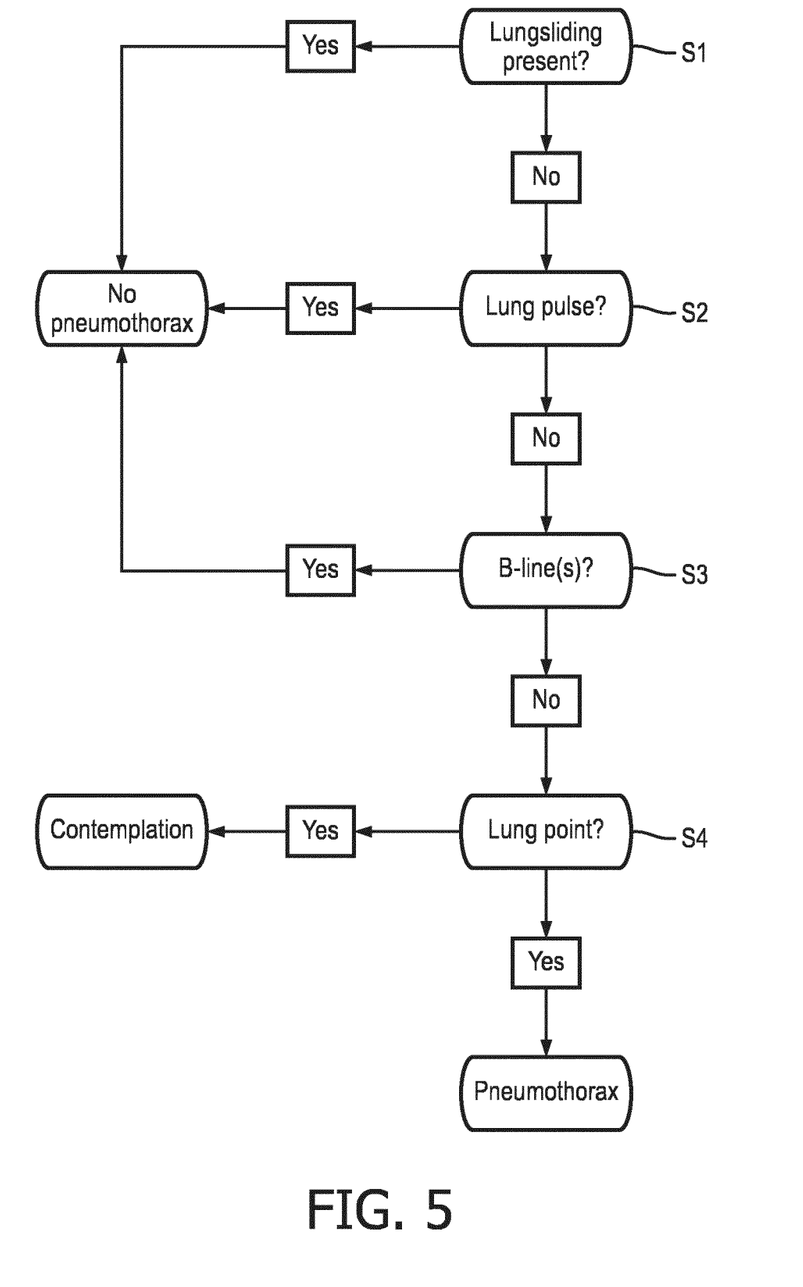
FIG. 5 illustrates a flowchart of a PTX detection method according to an embodiment of the present invention.

FIG. 5 illustrates a flowchart of a PTX detection method according to an embodiment of the present invention. As illustrated in FIG. 5, the step of detection of the presence of lung sliding S1, the step of detection of the presence of lung pulse S2, or the step of detection of the presence of B-line S3 are performed. If one of the presence of lung sliding, lung pulse or B-line is detected, it means there is no PTX at this portion of the chest. The indication IDA indicating completion of the PTX detection is generated. The indicator 107 indicates accordingly to the operator. In this scenario, the indication to the operator is to move the ultrasound probe 101 to the next portion of the chest immediately after any one of the presence of lung sliding, lung pulse or B-line is detected.

When the presence of none of lung sliding, lung pulse or B-line is detected, the step of detection of the presence of lung point S4 is to be further performed by means of the algorithm, as illustrated in FIG. 5. In sequence, the indication IDA indicating completion of a PTX detection is generated. The user interface 107 accordingly presents the indication IDA to the operator. In this scenario, the indication to the operator is to move the ultrasound probe 101 to the next portion of the chest immediately after the lung point is detected.

At different portions of the chest, the time required for PTX detection may be different. A portion of the chest where PTX is detected normally takes up more time than a PTX-free portion of the chest. The decision of ruling out PTX may be made quickly as long as a detection of one of the features is absent, for example, lung sliding, lung-pulse, or B-lines as illustrated in FIG. 5. There is no need to acquire ultrasound data at each portion of the chest for at least one full breathing cycle to reach a decision about absence of PTX, which results in a saving of time at the portion the chest. Thus, by means of the user interface 107, the operator is able to move the ultrasound probe 101 to the next portion of the chest in response to the indication IDA presented by the user interface 107, thereby spending less time at each portion of the chest.

As illustrated in FIG. 1, in another embodiment, the ultrasound system 100 may further comprise a reporting module 108, the processor 103 is configured to deliver a result of the predetermined procedure for a region of interest, the reporting module 108 is configured to identify a current region of interest of the at least one region of interest in accordance with a predetermined order of the at least one region of interest and record a result delivered by the processor 103 as a result for the current region of interest, the at least one region of interest comprising a plurality of regions of interest.

FIG. 6 illustrates an example of a plurality of regions of interest according to an embodiment of the invention. The ultrasound probe 101 is required to be placed on the plurality of regions of interest according to the predefined order of the clinical protocol. The predefined order may be shown by the user interface 107 and will be followed by all the operators. Referring to FIG. 6, the plurality of region of interest are a plurality of regions separated by lines along horizontal and vertical directions. The numbers shown in FIG. 6 indicate the order in which the ultrasound probe 101 is to be placed on the plurality of regions of interest, which is the predefined order. For each region of interest, there is a corresponding order in the sequence of the plurality of regions of interest.

Figure 7:
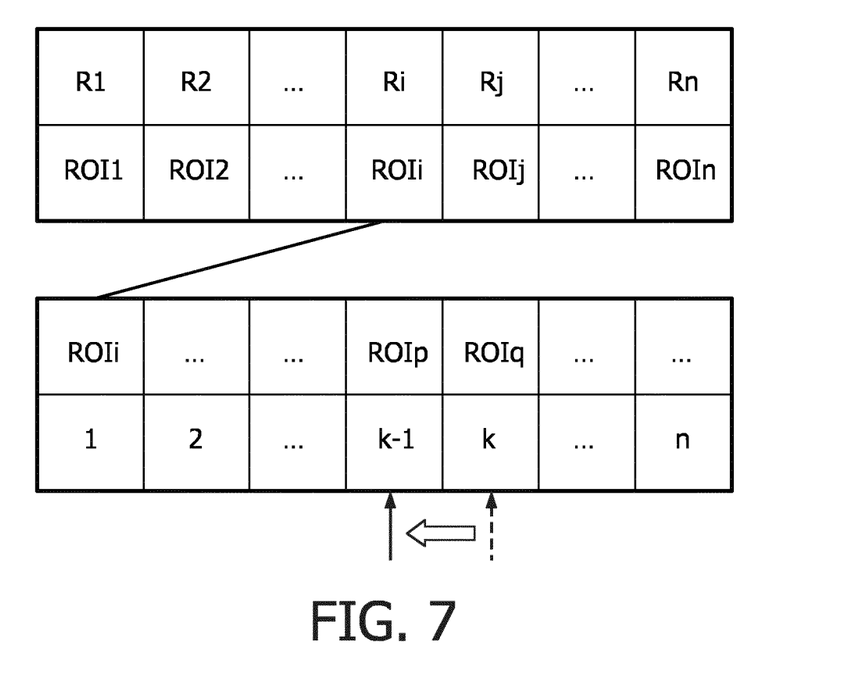
FIG. 7 illustrates an example of sequential results recorded according to an embodiment of the present invention.

The operator sequentially place the ultrasound probe 101 on the plurality of regions of interest and the processor 103 sequentially performs the predetermined procedure for the plurality of regions of interest. The reporting module 103 will identify the current region of interest as the first region of the plurality regions of interest when the ultrasound system 100 starts checking a certain subject and it is the first time that the motion signal MS generated by the motion sensor 102 indicates that the ultrasound probe 101 is stationary. Similarly, the reporting module 103 will identify the current region of interest as the second region of the plurality regions of interest when it is the second time that the motion signal MS generated by the motion sensor 102 indicates that the ultrasound probe 101 is stationary. Similarly, the reporting module 103 will identify the current region of interest as the nth region of the plurality regions of interest when it is the nth time that the motion signal MS generated by the motion sensor 102 indicates that the ultrasound probe 101 is stationary. In this way, the sequence of each region of interest among the plurality of region of interest can be identified and then the corresponding result of each region of interest can be recorded in association with each region of interest. FIG. 7 illustrates an example of sequential results recorded according to an embodiment of the present invention. For a region of interest ROIi of the plurality of regions of interest, a corresponding result Ri is delivered, as illustrated in the upper part of FIG. 7. Moreover, there is a specific order number associated with the region of interest ROIi derived from the predefined order, which is 1 in this example, as illustrated in the lower part of FIG. 7. The reporting module 108 identifies the current region of interest ROIi from the plurality of regions of interest as the first region of interest. Consequently, the result Ri is associated with the identified current region of interest ROIi.

As illustrated in FIG. 1, in another embodiment, the ultrasound system 100 may further comprise the user interface 107 configured to visualize the results recorded by the reporting module 108.

The results recorded by the reporting module 108 may be visualized on the user interface 107 directly. Alternatively, the results may be mapped on pre-acquired information and visualized together with the pre-acquired information. The pre-acquired information may be anatomy information of the plurality of regions of interest, such as CT images, MR images, or anatomy models of the plurality of regions of interest.

As illustrated in FIG. 1, in another embodiment, the ultrasound system 100 further comprises the user interface 107 for receiving a user input to go back and a go-back module 105 configured to identify the current region of interest on the basis of the recorded results and the user input.

The user interface 107 enables the user to give an input to go back, for example, when the user feels the operation is not done properly or the operation is not satisfactory for a region of interest, the user may give an input to go back, i.e., not record the result for the region of interest. Based on the user input to go back, the go-back module 105 identifies the current region of interest and records the results.

For example, in FIG. 7, the results of the predetermined procedure for the plurality of regions of interest are recorded sequentially. The predetermined procedure for a region of interest ROIp is completed, the corresponding order of which is k-1 on the basis of the predefined order. Then, the ultrasound probe 101 is moved to the next region of interest according to the predefined order, whose order is k. Referring to FIG. 7, a region of interest ROIq is the current region of interest. If the go-back module 105 receives the user input to go back at this moment, then the region of interest ROIp becomes the current region of interest. Accordingly, the predetermined procedure is started all over again for the current ROI, such as ROIp in this embodiment.

In another embodiment, the ultrasound system 100 may further comprise a position verification module 110 configured to calculate a ratio between the size of the ultrasound acoustic shadow and the total area of a region of interest from the echo signals received from the region of interest and generate a position indicator by comparing the ratio with a predetermined threshold.

The embodiment is shown in FIG. 1. When the ultrasound probe 101 is placed at a region of interest, based on the comparison of the ratio with the predetermined threshold, the position verification module 110 generates the position indicator showing whether the ultrasound probe 101 is placed properly. If the position indicator shows the ultrasound probe 101 is not placed properly, the operator needs to change the position of the ultrasound probe 101 until the position indicator shows that the ultrasound probe 101 is placed properly. Then the ultrasound probe 101, the motion detector 102 and the processor 103 start operating.

The ultrasound acoustic shadow is formed when ultrasound signals are blocked by a portion of the living being, for example, a bone or bony structure. For example, when the ultrasound probe 101 is placed on the chest, the ultrasound signals generated by the ultrasound probe 101 are not able to pass through ribs. The ratio between the size of the ultrasound acoustic shadow and the total area of a region of interest indicates whether the ultrasound probe 101 is placed on the correct position. The larger is the ratio, the better is the position for placing the ultrasound probe 101.

For example, there are dark areas under the ribs in acquired ultrasound images. Therefore, one embodiment is provided to calculate the ratio by using the acquired ultrasound images. In this embodiment, the ratio between the size of the ultrasound acoustic shadow and the total area of a region of interest is represented by the ratio between the area of the ultrasound acoustic shadow and the total area of the ultrasound image frame. The width of an ultrasound image frame is the width of the ultrasound probe 101, which can be measured directly. The depth of an ultrasound image frame is determined by the operator before the operation. Therefore, the total area of the ultrasound image frame is calculated by multiplying the width of the ultrasound image frame and the depth of the ultrasound image frame.

The area of the ultrasound acoustic shadow may be determined by applying a known image processing algorithm to the ultrasound image frame, for example, detecting the edge to identify the range of the ultrasound acoustic shadow and then calculate the area of the identified range.

The predetermined threshold is chosen in the range of [1/4-1/3] based on experimental results. A ratio smaller than the predetermined threshold indicates that the ultrasound probe 101 is placed at a proper position. A ratio larger than the predetermined threshold indicates that the ultrasound probe 101 is not placed at a proper position.

In another embodiment of the system 100, the motion sensor 102 is an accelerometer.

The accelerometer may be a 3-axis accelerometer, adapted to detect acceleration in any of three orthogonal directions. For example, a first axis of the accelerometer may be disposed in an x-direction, a second axis may be disposed in a y-direction, and a third axis may be disposed in a z-direction. By combining signals from each of the three axes, the accelerometer may be able to detect accelerations in any three-dimensional direction. By integrating accelerations occurring over a period of time, the processor may generate an accurate real-time velocity of the accelerometer on the basis of data from the accelerometer.

Figure 8:
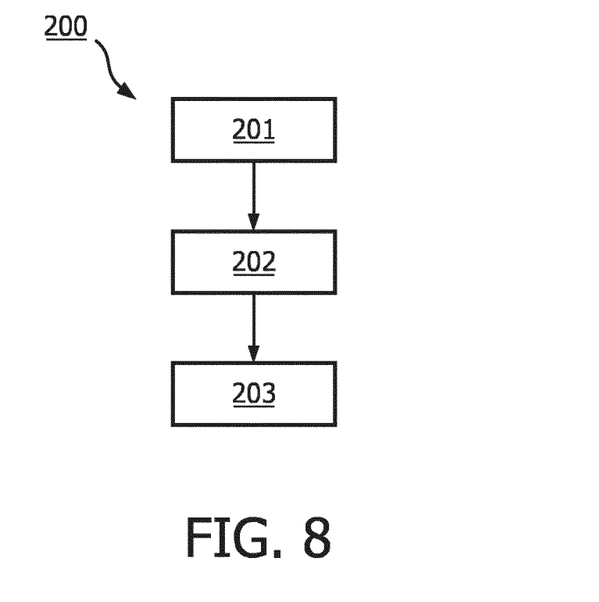
FIG. 8 schematically depicts a flowchart of a method according to an embodiment of the present invention.

FIG. 8 schematically depicts a flowchart of a method according to the present invention.

An ultrasound method 200 for sequentially performing a predetermined procedure for each of at least one region of interest, comprises a step of transmitting 201 a first ultrasound signal SG1 towards a region of interest and receiving echo signals from the region of interest. The ultrasound method 200 also comprises a step of detecting 202 a motion of an ultrasound probe 101 and generating a motion signal MS for indicating the motion of the ultrasound probe 101. The ultrasound method 200 also comprises a step of performing 203 a predetermined procedure for a region of interest on the basis of the echo signals received from the region of interest if the motion signal MS indicates that the ultrasound probe 101 is stationary.

In an embodiment, the ultrasound method 200 may further comprise a step of starting to transmit the first ultrasound signals SG1 if the motion signal MS indicates that the ultrasound probe 101 is stationary.

In an embodiment, the ultrasound method 200 may further comprise a step of transmitting a second ultrasound signals SG2 prior to transmitting the first ultrasound signal SG1.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An ultrasound system, comprising:
   an ultrasound probe;
   a motion sensor coupled to the ultrasound probe and configured to detect a motion of the ultrasound probe and generate a plurality of motion signals for indicating the motion of the ultrasound probe, wherein the ultrasound probe is configured to transmit a first ultrasound signal towards a first region of interest and receive first echo signals from the first region of interest when a first motion signal of the plurality of motion signals indicates that the ultrasound probe is stationary;
   a processor configured to perform a predetermined procedure for the first region of interest on the basis of the echo signals received from the first region of interest when the first motion signal indicates that the ultrasound probe is stationary, wherein the predetermined procedure comprises:
   extracting features of the first region of interest from the echo signals received from the first region of interest;
   determining, based on the features extracted, whether at least one of a lung sliding, a lung pulse, or a B-line are present in the first region of interest; and
   delivering a result indicating no pneumothorax is present in the first region of interest when at least one of the lung sliding, the lung pulse, or the B-line is determined to be present or delivering a result indicating pneumothorax is present in the first region of interest when none of the lung sliding, the lung pulse, and B-line are determined to be present,
   wherein the processor is further configured to generate an indication indicative of completion of the predetermined procedure, wherein the indication further indicates a second region of interest to transmit second ultrasound signals and receive second echo signals with the ultrasound probe when a second motion signal of the plurality of motion signals indicates that the ultrasound probe is stationary; and
   a user interface configured to present the indication.

2. An ultrasound system as claimed in claim 1, wherein the ultrasound probe is configured to transmit a third ultrasound signal prior to transmitting the first ultrasound signal.

3. An ultrasound system as claimed in claim 1, further comprising:
   a position verification module comprising a second processor configured to calculate a ratio between a size of the ultrasound acoustic shadow and a total area of the first region of interest from the echo signals received from the first region of interest and generate a position indicator by comparing the ratio with a predetermined threshold, wherein the position indicator indicates the ultrasound probe is placed properly when the ratio is below the predetermined threshold and indicates the ultrasound probe is placed improperly when the ratio is equal to or greater than the predetermined threshold.

4. An ultrasound system as claimed in claim 1, wherein the motion sensor comprises at least one of an accelerometer, a gyroscope, a barometer, a camera, or a global positioning system sensor.

5. An ultrasound system as claimed in claim 1, wherein the indication is provided by a light indicator comprising different colors of the user interface.

6. An ultrasound system as claimed in claim 1, wherein the indication is provided by an icon on a display of the user interface.

7. An ultrasound system as claimed in claim 1, wherein the indication is provided as audio instructions by the user interface.

8. An ultrasound system as claimed in claim 1, further comprising a reporting module comprising a second processor, wherein the processor is configured to deliver the result of the predetermined procedure for a plurality of regions of interest including the first region of interest and the second region of interest to the reporting module, wherein the reporting module is configured to identify a current region of interest of the plurality of regions of interest in accordance with a predetermined order of at least one region of interest of the plurality of regions of interest for which results are to be recorded and record the result delivered by the processor as a result for the current region of interest.

9. An ultrasound system as claimed in claim 8, wherein the user interface is further configured to visualize results for ones of the plurality of regions of interest recorded by the reporting module.

10. An ultrasound system as claimed in claim 8, wherein the user interface is further configured to receive a user input to not record the result for the current region of interest; and the system further comprises a go-back module comprising a third processor configured to identify the current region of interest on the basis of the recorded results and the user input.

11. An ultrasound method comprising the steps of:
displaying, on a user interface, a plurality of regions of interest according to a predefined order;
detecting, with a motion sensor, a motion of an ultrasound probe coupled to the motion sensor and generate a first motion signal of a plurality of motion signals for indicating the motion of the ultrasound probe;
responsive to the motion signal indicating the ultrasound probe is stationary:
  transmitting, with the ultrasound probe, a first ultrasound signal towards a first region of interest of the plurality of regions of interest and receiving first echo signals from the first region of interest; and
  performing, with a processor, a predetermined procedure for the first region of interest on the basis of the first echo signals received from the first region of interest, wherein the predetermined procedure comprises:
    extracting features of the first region of interest from the first echo signals received from the region of interest;
    determining, based on the features extracted, whether at least one of a lung sliding, a lung pulse, or a B-line are present in the first region of interest;
    delivering a result indicating no pneumothorax is present in the first region of interest when at least one of the lung sliding, the lung pulse, or the B-line is determined to be present or delivering a result indicating pneumothorax is present in the first region of interest when none of the lung sliding, the lung pulse, and B-line are determined to be present;
  providing, via the user interface, an indication indicative of completion of the predetermined procedure, wherein the indication further indicates a second region of interest of the plurality of regions of interest to transmit second ultrasound signals and receive second echo signals with the ultrasound probe when a second motion signal of the plurality of motion signals indicates that the ultrasound probe is stationary.

12. An ultrasound method as claimed in claim 11, further comprising a step of transmitting a third ultrasound signal prior to transmitting the first ultrasound signal.

* * * * *